US012521536B2

(12) United States Patent
Presteng et al.

(10) Patent No.: US 12,521,536 B2
(45) Date of Patent: Jan. 13, 2026

(54) EXPANDABLE DILATOR

(71) Applicant: BOSTON SCIENTIFIC SCIMED, INC., Maple Grove, MN (US)

(72) Inventors: Daniel Presteng, Santa Clara, CA (US); James M. Anderson, Corcoran, MN (US); John M. Edgell, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 49 days.

(21) Appl. No.: 18/742,240

(22) Filed: Jun. 13, 2024

(65) Prior Publication Data

US 2024/0415540 A1 Dec. 19, 2024

Related U.S. Application Data

(60) Provisional application No. 63/472,863, filed on Jun. 14, 2023.

(51) Int. Cl.
*A61M 29/00* (2006.01)

(52) U.S. Cl.
CPC .................................. *A61M 29/00* (2013.01)

(58) Field of Classification Search
CPC ....... A61B 17/3439; A61B 2017/3433; A61M 2025/0675; A61M 25/0668; A61M 2025/0024; A61M 29/00; A61M 25/0023
See application file for complete search history.

(56) References Cited

U.S. PATENT DOCUMENTS

| | | | | |
|---|---|---|---|---|
| 5,259,366 | A | 11/1993 | Reydel et al. | |
| 8,845,726 | B2 | 9/2014 | Tebbe et al. | |
| 10,143,491 | B2 | 12/2018 | Clancy et al. | |
| 11,129,959 | B2 | 9/2021 | Hart et al. | |
| 11,191,927 | B2 | 12/2021 | McLaughlin et al. | |
| 11,364,118 | B2 | 6/2022 | Kheradvar | |
| 2006/0264972 | A1* | 11/2006 | Mulholland | A61M 25/0068 606/108 |
| 2009/0299451 | A1* | 12/2009 | Ellsworth | A61F 2/82 623/1.11 |

(Continued)

FOREIGN PATENT DOCUMENTS

| | | | |
|---|---|---|---|
| EP | 2241347 | A2 | 10/2010 |
| EP | 3251634 | A1 | 12/2017 |

OTHER PUBLICATIONS

Invitation To Pay Additional Fees and, Where Applicable, Protest Fee for International Application PCT/US2024/033810, dated Oct. 15, 2024. (13 Pages).

*Primary Examiner* — Katherine M Sh

(74) *Attorney, Agent, or Firm* — Seager, Tufte & Wickhem LLP

(57) ABSTRACT

An expandable dilator for use with an expandable sheath includes a shaft having a tapered distal tip, a body, a proximal end, and a lumen extending longitudinally from the distal tip to the proximal end. The expandable dilator includes an expansion mechanism extending radially outward from the outer surface of the shaft. When the expandable dilator is withdrawn proximally into the expandable sheath, the expansion mechanism engages the distal end of the sheath and expands the sheath as the expansion mechanism moves proximally through the sheath.

20 Claims, 17 Drawing Sheets

(56) References Cited

U.S. PATENT DOCUMENTS

| | | | | |
|---|---|---|---|---|
| 2011/0190697 A1* | 8/2011 | Farnan | .............. | A61M 25/0662 604/99.01 |
| 2012/0083740 A1* | 4/2012 | Chebator | .......... | A61M 25/0074 604/164.03 |
| 2023/0398330 A1* | 12/2023 | Mitze | .................. | A61M 25/005 |

* cited by examiner

EXPANDABLE DILATOR

CROSS-REFERENCE TO RELATED APPLICATIONS

This application claims the benefit of priority of U.S. Provisional Application No. 63/472,863 filed Jun. 14, 2023, the entire disclosure of which is hereby incorporated by reference.

TECHNICAL FIELD

The disclosure pertains to medical devices and more particularly to expandable introducers and dilators, and methods for using such medical devices.

BACKGROUND

A wide variety of medical devices have been developed for medical use including, for example, medical devices utilized to deliver and implant artificial heart valves. These medical devices may be used in a variety of implantation procedures, and are manufactured and used according to any one of a variety of different methods. Of the known medical devices and methods, each has certain advantages and disadvantages. There is an ongoing need to provide alternative medical devices as well as alternative methods for manufacturing and using the medical devices.

SUMMARY

This disclosure provides design, material, manufacturing method, and use alternatives for medical devices. An example expandable dilator includes a shaft having a tapered distal tip, a body, a proximal end, and a lumen extending longitudinally from the tapered distal tip to the proximal end, the shaft including a cutout through a sidewall of the shaft adjacent the tapered distal tip, and a slit extending through the sidewall and extending from the cutout to the proximal end, an expander positioned within the cutout, the expander having an outer diameter larger than an inner diameter of the lumen such that a portion of the expander extends through the cutout, the expander including a tether fixed to the expander and extending through the lumen and exiting out the proximal end of the shaft, and wherein pulling the tether proximally moves the expander proximally through the shaft such that the expander separates opposing edges of the slit as the expander moves proximally through the shaft.

Alternatively or additionally to the embodiment above, a proximal end of the tether is fixed to a knob coupled to the proximal end of the shaft, the knob configured to pull the tether and the expander proximally through the shaft.

Alternatively or additionally to any of the embodiments above, the knob is configured to be pulled proximally away from the proximal end of the shaft.

Alternatively or additionally to any of the embodiments above, the knob is coupled to the shaft with a frangible connector that is breakable with a twisting or pulling force.

Alternatively or additionally to any of the embodiments above, the knob is rotatably coupled to the proximal end of the shaft, and the tether is fixed to the knob such that rotation of the knob relative to the shaft in a first direction winds the tether onto the knob as the expander is pulled proximally through the lumen.

Alternatively or additionally to any of the embodiments above, the shaft includes a plurality of channels extending longitudinally along an entirety of the shaft from a proximal end of the tapered distal tip.

An example dilation system includes the above expandable dilator and an expandable sheath having a distal end, a proximal end, a lumen extending therebetween, and at least one fold extending longitudinally from the distal end to the proximal end, each fold defined by a circumferential overlap of material forming the expandable sheath, the expandable sheath including a distal ring configured to hold the expandable sheath in a compressed configuration, the distal ring having a longitudinal slit disposed over the fold, the distal ring biased in a closed configuration and expandable to an expanded configuration in which the slit is expanded when the expandable dilator is disposed within the expandable sheath with the expander positioned distal of the distal end of the expandable sheath, and the expander of the expandable dilator is pulled proximally, thereby allowing the fold to unfold and expand an inner diameter of the expandable sheath.

Another example dilator for use with an expandable sheath includes a shaft having a tapered distal tip, a proximal end, a flexible ring disposed around the tapered distal tip, the flexible ring configured to be moved axially from the tapered distal tip onto the shaft, the flexible ring having a plurality of protrusions extending radially outward from an outer surface of the flexible ring, and at least one tether having a distal end fixed to the flexible ring and a proximal end extending axially along an outer surface of the tapered distal tip and into an opening in the shaft, the tether extending through a lumen of the shaft, wherein the proximal end of the at least one tether extends proximally out of the proximal end of the shaft.

Alternatively or additionally to the embodiment above, the at least one tether includes two tethers fixed to opposite sides of the flexible ring, wherein the opening in the shaft includes two openings disposed on opposite sides of the shaft, wherein each tether extends into one of the two openings.

Alternatively or additionally to any of the embodiments above, the plurality of protrusions are ridges extending longitudinally along the outer surface of the flexible ring.

Alternatively or additionally to any of the embodiments above, the opening is disposed on the shaft such that when the flexible ring is pulled onto the shaft, the opening is adjacent a proximal end of the flexible ring.

A further example expandable dilator for use with an expandable sheath includes a shaft having a tapered distal tip and a body with a proximal end, and a lumen extending longitudinally therethrough, at least one expandable member disposed on the body of the shaft, each expandable member configured to move from a compressed configuration to an expanded configuration, wherein when in the compressed configuration an outer diameter of the expandable member is equal to or less than an outer diameter of the body, wherein when in the expanded configuration the outer diameter of the expandable member is greater that the outer diameter of the body, and wherein when the shaft is disposed within the expandable sheath, the expandable member is in the compressed configuration, and moving the shaft distally out of the expandable sheath causes the expandable member to move into the expanded configuration.

Alternatively or additionally to the embodiment above, the shaft includes at least one recess on the body, and the expandable member extends over the recess.

Alternatively or additionally to any of the embodiments above, the expandable member is formed of a shape memory material and is biased in the expanded configuration.

Alternatively or additionally to any of the embodiments above, the recess includes a spring and the expandable member extends over the spring.

Alternatively or additionally to any of the embodiments above, the shaft includes at least one rotational marker on the proximal end indicating a circumferential position of the expandable member.

Alternatively or additionally to any of the embodiments above, the expandable member includes a compressible ring disposed between the tapered distal tip and the body, the shaft including a tether fixed to an inner wall of the tapered distal tip and extending through the lumen and out the proximal end of the shaft, wherein pulling the tether proximally relative to the shaft pulls the tapered distal tip towards a distal end of the body and compresses the compressible ring such that an outer diameter of the compressible ring extends radially outward beyond an outer surface of the body, forming a circumferential ridge.

Alternatively or additionally to any of the embodiments above, the expandable dilator further includes a knob coupled to the proximal end of the shaft, the knob configured to pull the tether proximally relative to the shaft.

Alternatively or additionally to any of the embodiments above, the knob is coupled to the proximal end of the shaft with a frangible connector that is breakable with a twisting or pulling force wherein the knob is configured to be pulled proximally away from the proximal end of the shaft.

Alternatively or additionally to any of the embodiments above, the knob is rotatably coupled to the proximal end of the shaft, and the tether is fixed to the knob such that rotation of the knob relative to the shaft in a first direction winds the tether onto the knob as the tapered distal tip is pulled proximally.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description of various embodiments in connection with the accompanying drawings, in which.

Figure 1:
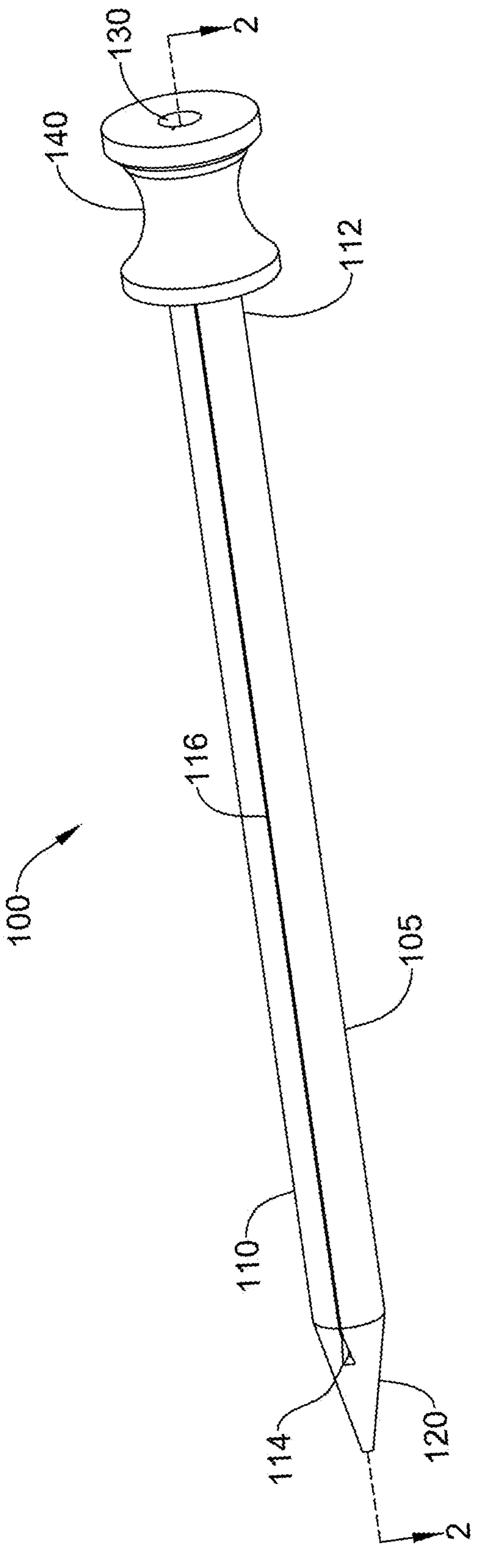
FIG. 1 is a perspective view of an example expandable dilator.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5). Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosure are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "withdraw", variants thereof, and the like, may be generally considered with respect to the positioning, direction, and/or operation of various elements relative to a user/operator/manipulator of the device, wherein "proximal" and "withdraw" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as “upstream”, “downstream”, “inflow”, and “outflow” refer to a direction of fluid flow within a lumen, such as a body lumen, a blood vessel, or within a device.

The term “extent” may be understood to mean a greatest measurement of a stated or identified dimension, unless the extent or dimension in question is preceded by or identified as a “minimum”, which may be understood to mean a smallest measurement of the stated or identified dimension. For example, “outer extent” may be understood to mean a maximum outer dimension, “radial extent” may be understood to mean a maximum radial dimension, “longitudinal extent” may be understood to mean a maximum longitudinal dimension, etc. Each instance of an “extent” may be different (e.g., axial, longitudinal, lateral, radial, circumferential, etc.) and will be apparent to the skilled person from the context of the individual usage. Generally, an “extent” may be considered a greatest possible dimension measured according to the intended usage, while a “minimum extent” may be considered a smallest possible dimension measured according to the intended usage. In some instances, an “extent” may generally be measured orthogonally within a plane and/or cross-section, but may be, as will be apparent from the particular context, measured differently—such as, but not limited to, angularly, radially, circumferentially (e.g., along an arc), etc. Additionally, the term “substantially” when used in reference to two dimensions being “substantially the same” shall generally refer to a difference of less than or equal to 5%.

The terms “monolithic” and “unitary” shall generally refer to an element or elements made from or consisting of a single structure or base unit/element. A monolithic and/or unitary element shall exclude structure and/or features made by assembling or otherwise joining multiple discrete elements together.

It is noted that references in the specification to “an embodiment”, “some embodiments”, “other embodiments”, etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to affect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a “first” element may later be referred to as a “second” element, a “third” element, etc. or may be omitted entirely, and/or a different feature may be referred to as the “first” element. The meaning and/or designation in each instance will be apparent to the skilled practitioner.

The following description should be read with reference to the drawings, which are not necessarily to scale, wherein similar elements in different drawings are numbered the same. The detailed description and drawings are intended to illustrate but not limit the disclosure. Those skilled in the art will recognize that the various elements described and/or shown may be arranged in various combinations and configurations without departing from the scope of the disclosure. The detailed description and drawings illustrate example embodiments of the disclosure. However, in the interest of clarity and ease of understanding, while every feature and/or element may not be shown in each drawing, the feature(s) and/or element(s) may be understood to be present regardless, unless otherwise specified.

In some instances, performing percutaneous medical procedures may require the insertion, inflation, deflation, and withdrawal of a balloon through an introducer sheath. For example, prior to some transcatheter aortic valve replacement (TAVR) procedures, a balloon valvuloplasty (BAV) may be done which is inserted and withdrawn through the introducer sheath prior to expansion which occurs during the TAVR delivery. In some cases there may be problems withdrawing the BAV device through an unexpanded introducer sheath distal tip. For example, the balloon may not deflate to its pre-inflation dimensions, which may cause problems when the deflated balloon is withdrawn into the introducer sheath. In some cases, the deflated balloon may cause the distal end of the introducer sheath to bunch up or otherwise be deformed. Some introducer sheaths may be expandable to allow for relatively large medical devices to be delivered therethrough. These expandable sheaths may be configured to expand as the large medical device is moved distally through them, however, when a deflated balloon is withdrawn proximally into the distal end of the expandable sheath, it may be desirable to provide a mechanism to expand the sheath to allow the balloon to enter the distal end of the sheath without damaging the sheath. In many instances, a dilator is used during insertion of the introducer sheath. The following examples illustrate various mechanisms for expanding an expandable sheath in a distal to proximal direction from the distal end. A modified combination dilator and expander feature may provide the desired expansion of the distal end of the expandable sheath without the need for inserting a secondary tool to enable expansion.

Figure 2:
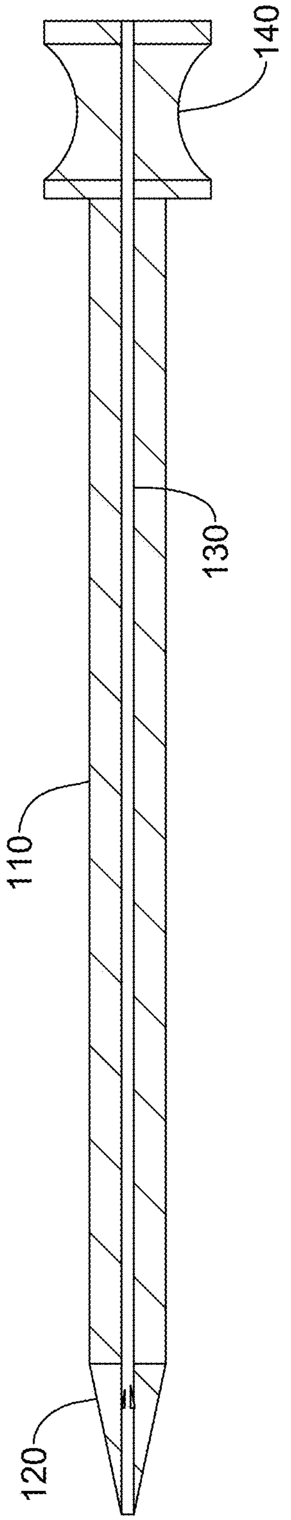
FIG. 2 is a side cross-sectional view taken along line 2-2 of FIG. 1.

FIG. 1 illustrates an example dilator 100, including a shaft 105 having a tapered distal tip 120, a body 110, and a proximal end 112. A knob 140 may be coupled to the proximal end 112 of the body 110, and a lumen 130 may extend longitudinally from the distal tip to the proximal end of the knob 140. The shaft 105 may include a cutout 114 through a sidewall of the shaft adjacent the distal tip, and a slit 116 may extend through the sidewall and extend from the cutout 114 to the proximal end 112 of the shaft 105. In the embodiment shown, the cutout 114 is located on the tapered distal tip 120. The lumen 130 may extend completely through the distal tip 120 and the body 110. See FIG. 2. The lumen 130 may also extend at least partially through or completely through the knob 140.

Figure 3:
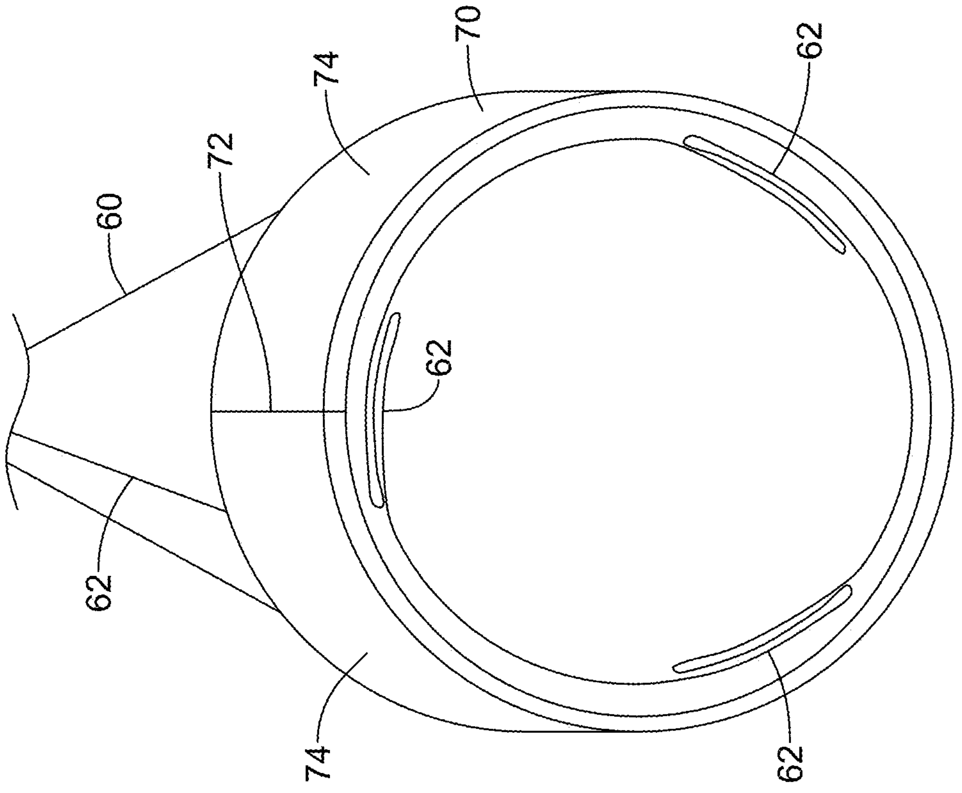
FIG. 3 is an end perspective view of an example expandable sheath.

FIG. 3 shows an example expandable sheath 60 for use with any of the dilators described herein. The expandable sheath 60 may have one or more folds 62 that allow for circumferential expansion of the sheath. Each fold 62 includes a circumferential overlap of the material forming the sheath, with the fold 62 extending longitudinally along the sheath 60. In some examples, the fold 62 may extend along the entire length of the sheath 60. In some examples, a separating ring 70 may be coupled to the distal end of the sheath, extending over the entire circumference of the sheath to hold the sheath 60 in a compressed configuration. The ring 70 may include one or more longitudinal slits 72 to allow for separation of sections 74 of the ring 70 and the expansion of the sheath 60. The slits 72 may be disposed over the folds 62. The sections 74 of the ring 70 may be secured to the sheath 60, allowing the sheath to expand at each fold 62 as the sections 74 separate when a radially outward force is applied to the inner surface of the sheath. The ring 70 may be biased in a closed configuration, with the slits 72 being closed and the folds 62 in their overlapped configuration. When a medical device, such as a replacement heart valve, is moved distally through the expandable sheath 60, the medical device may apply a radially outward force to temporarily expand the sheath as the device moves through the sheath. In some examples, the sheath may return to its original circumferential shape and size after the medical device moves distally through the sheath. In this way, the sheath 60 may be biased in a compressed and folded configuration. Additionally, the radially outward force may be applied by a dilator as described herein.

Figures 4A, 4B, 4C:
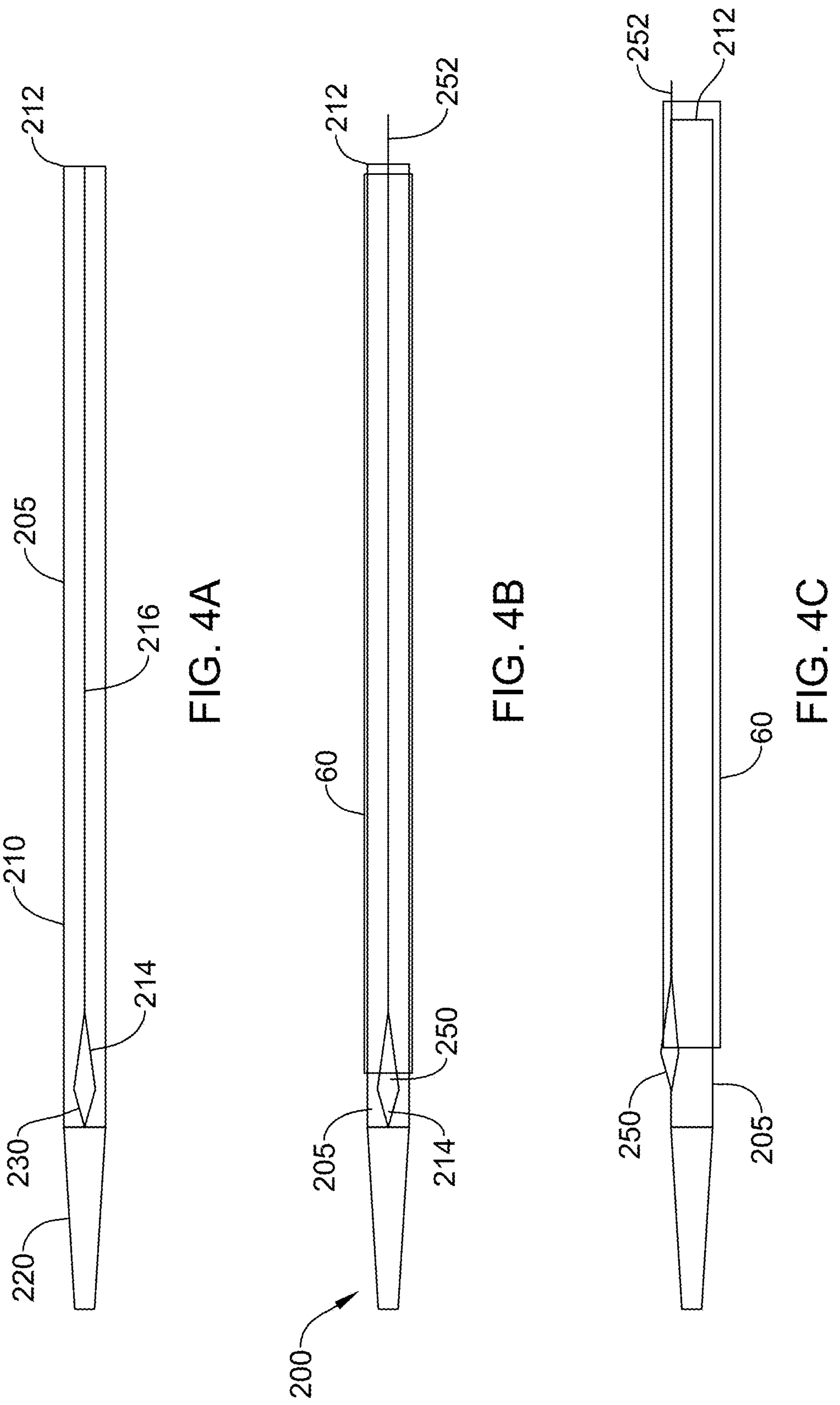
FIGS. 4A-4E are side views of another example expandable dilator during use.

FIG. 4A shows a side view of another example shaft 205. The cutout 214 is shown positioned immediately proximal of the tapered distal tip 220, on the body 210. The slit 216 extends through the sidewall of the body 210 from the cutout 214 to the proximal end 212 of the shaft 205. The cutout 214 and the slit 216 extend into the lumen 230 running the entire length of the shaft 205. In other embodiments, the cutout 114 may be disposed on the distal tip 120, as shown in FIG. 1. FIG. 4B shows a dilator 200 including the shaft 205 of FIG. 4A with an expander 250 positioned within the lumen 230 in the region of the cutout 214. The dilator 200 is shown without a knob, however it will be understood that a knob may be used on any of the dilators described herein. The expander 250 may have an outer diameter larger than an inner diameter of the shaft lumen such that a portion of the expander 250 extends through the cutout 114, as shown in FIG. 4C, which is a view rotated 90 degrees from the view in FIG. 4B. The expander 250 may include a tether 252 fixed to the expander and extending proximally through the lumen and exiting out the proximal end 212 of the shaft 205. The tether 252 may be a flexible wire.

Figure 4D:
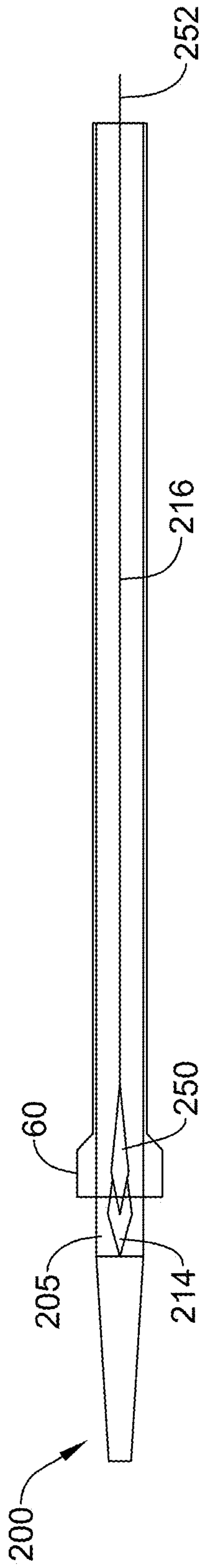
Figure 4E:
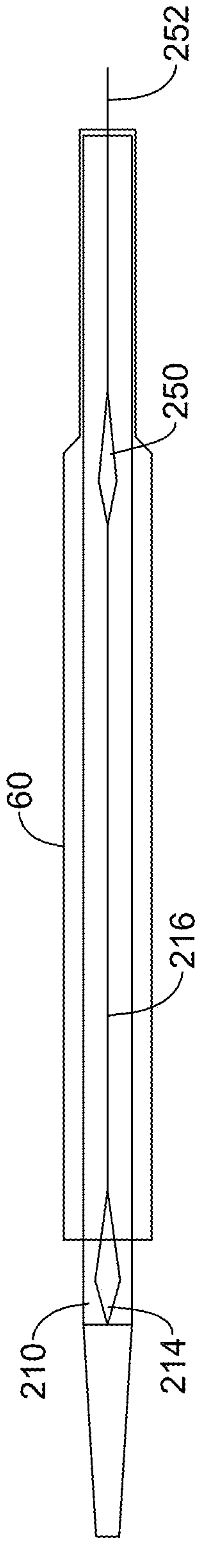
Figure 5A:
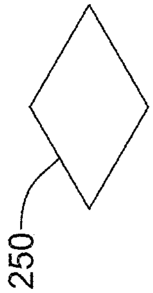
FIGS. 5A-5D are side views of example expander shapes.
Figure 5B:
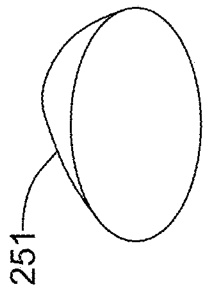
Figure 5C:
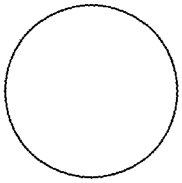
Figure 5D:
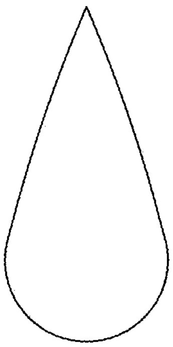

FIGS. 4B and 4C show the dilator 200 positioned inside an introducer sheath such as the expandable sheath 60 of FIG. 3. As described above, the expandable sheath 60 may have one or more circumferentially folds 62 extending longitudinally along the entire length of the sheath. When the dilator 200 is positioned within the expandable sheath 60 with the expander 250 disposed distal of the distal end of the expandable sheath, the folds may be in their folded configuration. In some examples, the shaft 205 may be rotated such that the expander 250 is positioned under a fold in the expandable sheath 60. FIG. 4D illustrates the initial expansion of the distal end of the sheath 60 as the tether 252 is pulled proximally relative to the shaft 205. As the expander 250 is pulled proximally from the cutout 214 through the shaft 205, the expander 250 separates the opposing edges of the slit 216, and unfolds the expandable sheath 60 as the expander 250 moves proximally through the shaft. See FIG. 4E. Alternatively, once the expander 250 is sitting proximal of the cutout 214, the entire dilator 200, including the shaft 205 and expander 250, may be pulled proximally through the sheath 60, thereby expanding the sheath 60. Expanding the sheath 60 allows any deflated balloon or other medical device positioned distally of the sheath 60 to be withdrawn proximally through the expanded sheath 60.

FIGS. 5A-5D illustrate a variety of shapes of expander 250 that may be used with the above dilators. Example shapes of the expander 250 may include diamond (FIG. 5A), oval (FIG. 5B), round (FIG. 5C), teardrop, (FIG. 5D), etc. Any of the round, oval, or teardrop expander 250 may include a fin 251 (FIG. 5B) positioned to extend through the cutout 214 to facilitate separation of the slit 216.

Figure 6:
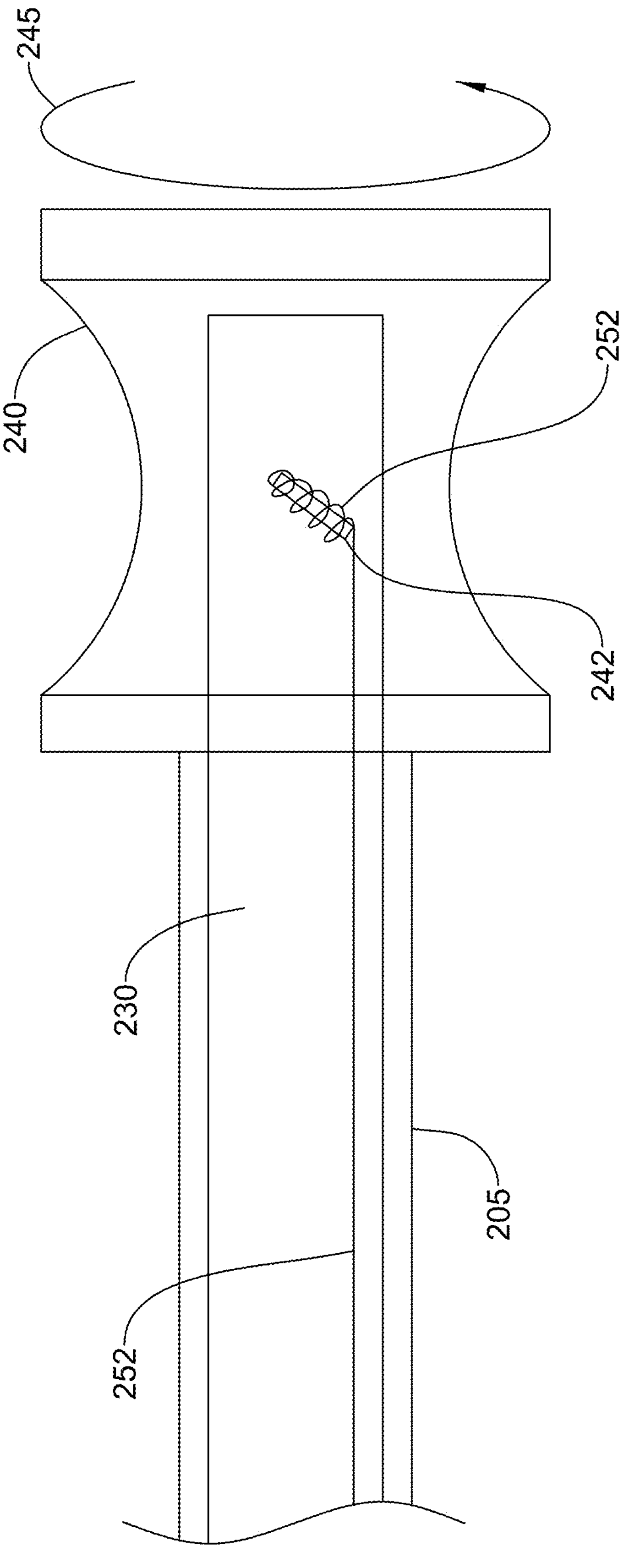
FIG. 6 is a side cross-sectional view of an example rotatable knob.
Figure 7:
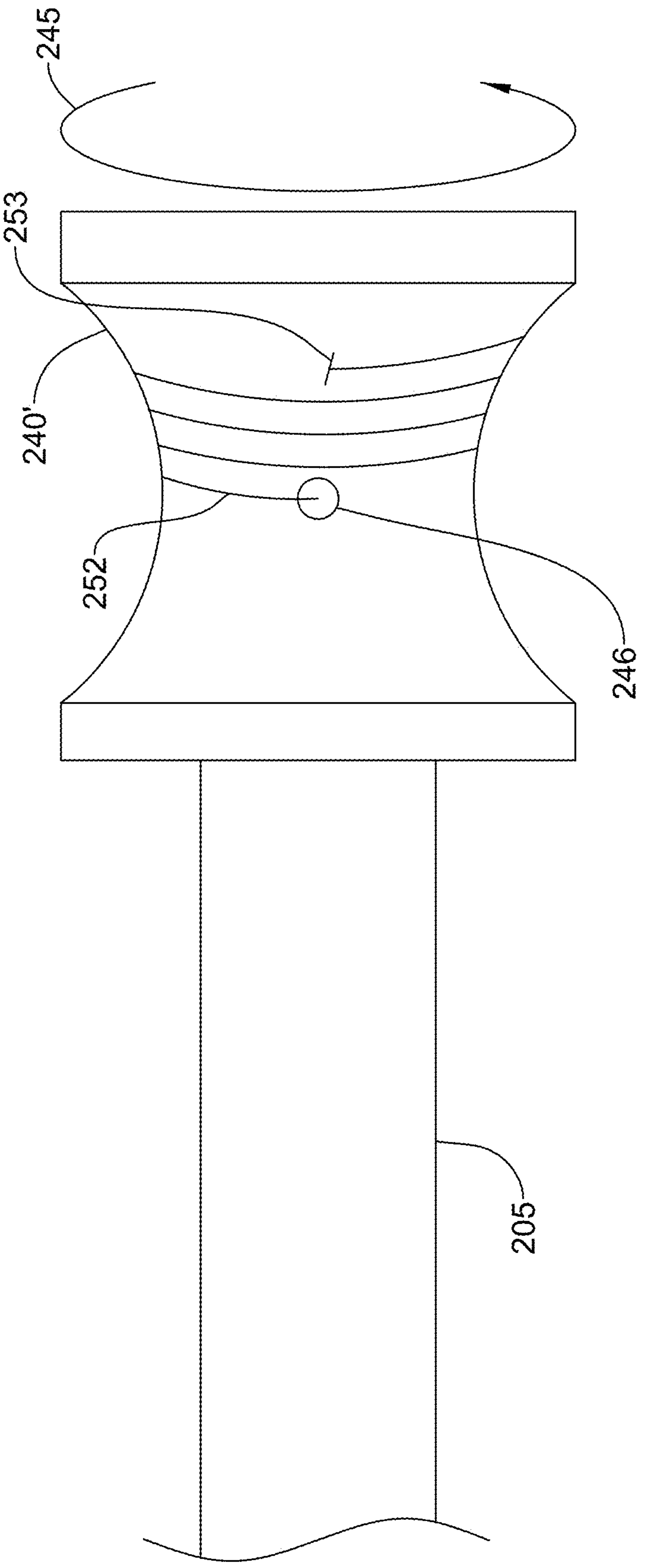
FIG. 7 is a side view of another example rotatable knob.

In the examples discussed above, the tether 252 may be pulled manually by grasping the proximal end and pulling while holding the shaft 205 stationary. In other examples, the dilator may include a knob 240 coupled to the proximal end of the shaft 205. In the example shown in FIG. 6, the knob 240 is rotatably coupled to the shaft 205 and the knob 240 has a continuation of the lumen 230 extending through the shaft 205. A pin 242 may be disposed across the lumen 230 within the knob 240, and a proximal end of the tether 252 may be fixed to the pin 242. Rotation of the knob 240, as indicated by arrow 245, winds the tether 252 around the pin 242 and pulls the tether 252 proximally, thereby pulling an expander attached to the distal end of the tether proximally through the shaft 205. In another example, as shown in FIG. 7, the tether 252 may extend through an opening 246 in the side of a knob 240' rotatably coupled to the proximal end of the shaft 205. The proximal end of the tether 252 may be fixed to the outer surface of the knob 240', such as with a staple 253 or adhesive. Rotation of the knob 240' relative to the shaft 205, as indicated by arrow 245, causes the tether 252 to be wound around the outer surface of the knob 240', as shown in FIG. 7.

Figure 8:
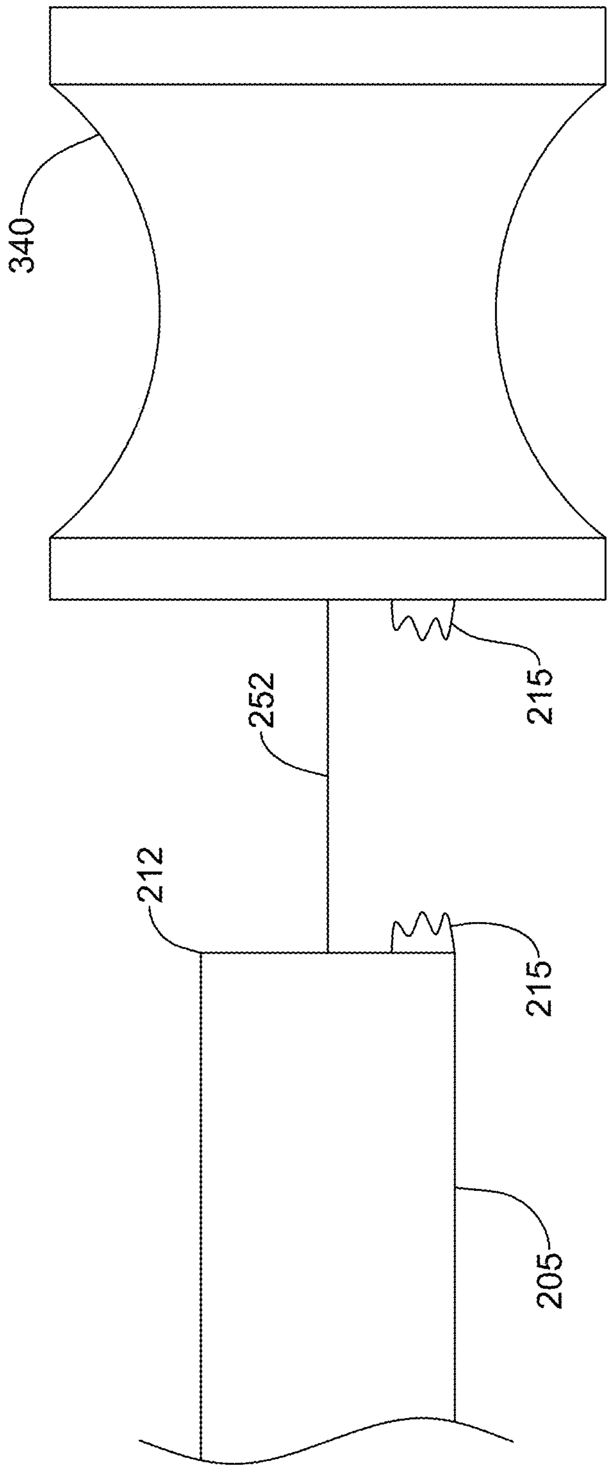
FIG. 8 is a side view of an example pull knob.

FIG. 8 illustrates another example of a dilator shaft 205 with a pull knob 340 configured to pull the tether 252 and expander proximally through the shaft. In this example, the proximal end of the tether 252 may be fixed to the knob 340. The knob 340 may have a lumen extending partially therethrough and the tether 252 may be fixed within the lumen. In other examples, the knob 340 may be solid and the tether 252 may be fixed to the distal end of the knob 340. The knob 340 may be configured to be pulled proximally away from the proximal end 212 of the shaft 205. In some examples, the knob 340 may be coupled to the shaft 205 with a frangible connector 215 that is breakable with a twisting or pulling force.

Figure 9A:
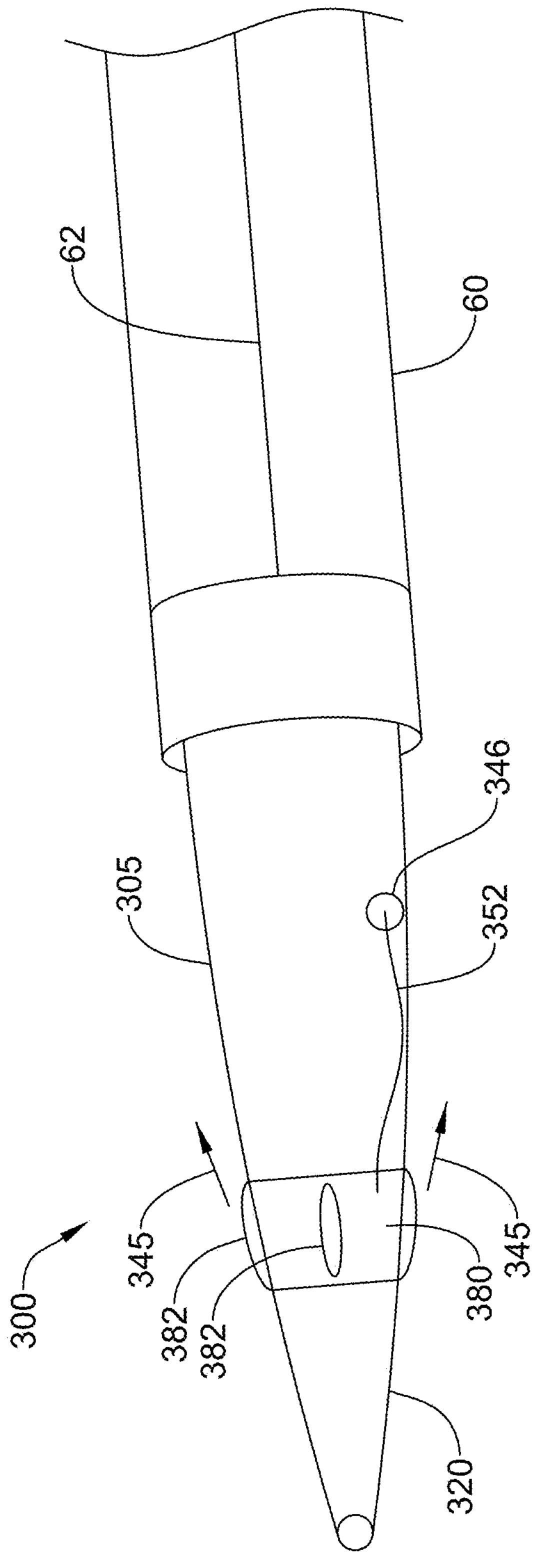
FIGS. 9A and 9B are side views of another example dilator with a flexible ring.
Figure 9B:
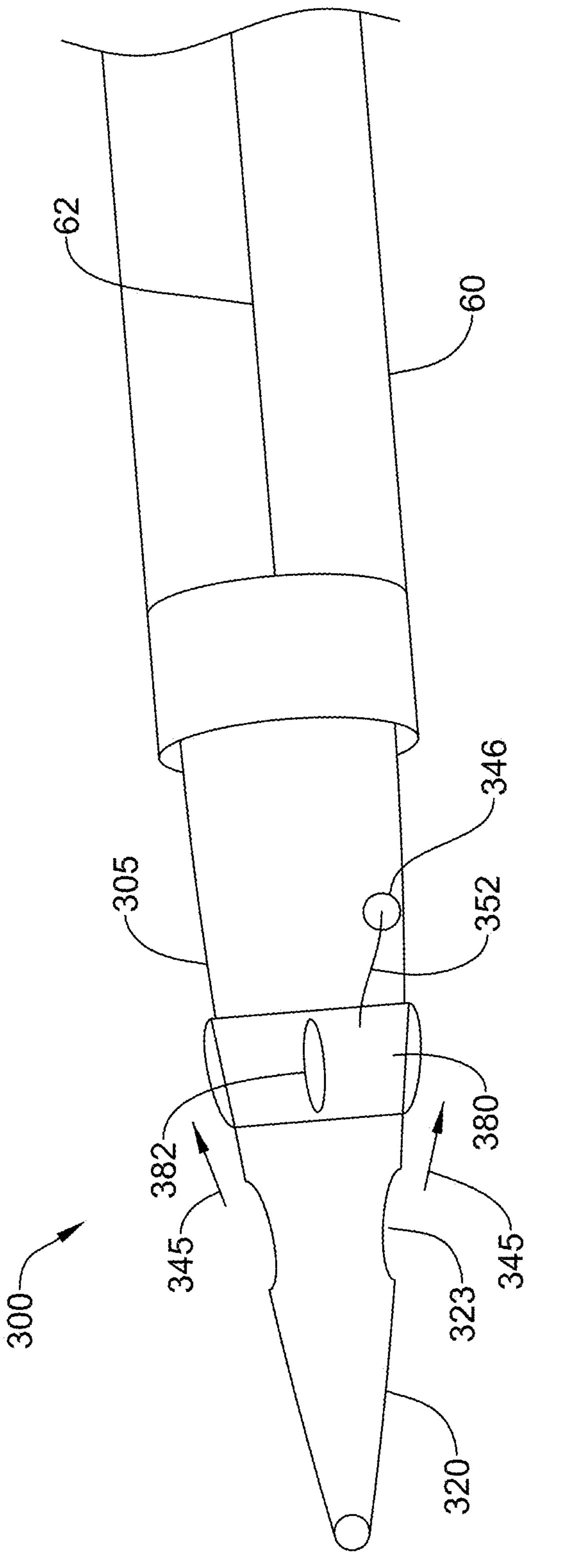

In another example, the dilator 300 may include a shaft 305 disposed within an expandable sheath 60 having one or more folds 62 as described above, and a flexible ring 380 with a plurality of protrusions 382 extending radially outward from an outer surface of the flexible ring. The flexible ring 380 may be configured to expand as it is moved axially from the tapered distal tip 320 onto the shaft 305, as indicated by arrows 345, shown in FIGS. 9A and 9B. The flexible ring 380 may be formed from an elastomeric material and may contain a radiopaque marker. In one example, the flexible ring 380 may be made of polyether block amide (PEBA) with tungsten so the ring is radiopaque. The PEBA may have a shore hardness of 35 D. When the dilator 300 is positioned within the sheath 60 described above, the protrusions 382 are configured to expand the folds 62 of the sheath 60. In some examples, the distal end of at least one tether 352 may be fixed to the flexible ring 380 and the tether 352 may extend through an opening 346 in the shaft 305 with the proximal end of the tether 352 extending out the proximal end of the shaft 305. Two tethers 352 fixed to opposite sides of the flexible ring 380 may provide for a balanced retraction of the ring. In some examples, the tapered distal tip 320 may include a recess 323 on the tapered distal tip 320 configured to receive the flexible ring 380, as shown in FIG. 9B. Pulling the tether(s) 352 proximally may pull the flexible ring 380 out of the recess 323 and onto the shaft 305. Each tether 352 may extend through a separate opening 346 in the shaft 305 with the proximal end of the tether 352 extending out the proximal end of the shaft 305. The tether(s) 352 may be manually pulled proximally relative to the shaft 305 to move the flexible ring 380 from the tapered distal tip 320 onto the shaft 305. See FIG. 9B. In other examples, the dilator 300 may include a knob as discussed above, either rotatably coupled to the shaft 305 or a pull knob configured to be pulled proximally, with the proximal end of the tether 352 fixed to the knob. With the flexible ring 380 positioned on the shaft 305, withdrawing the dilator 300 proximally through the sheath 60 may move the protrusions 382 into contact with the folds 62, pushing the folds to open thereby expanding the sheath 60 and allowing any deflated balloon or other medical device positioned distally of the sheath 60 to be withdrawn proximally through the expanded sheath 60.

Figure 10A:
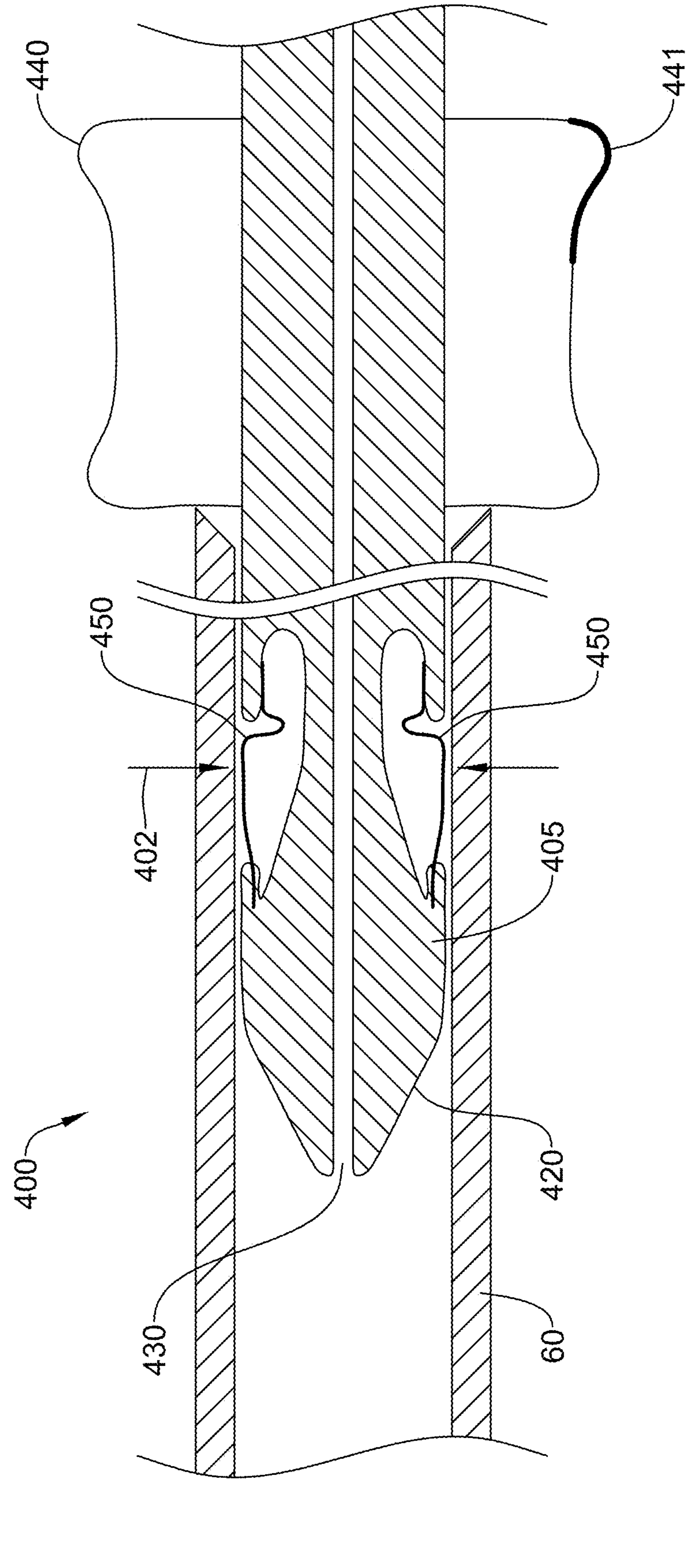
FIGS. 10A-10C are side cross-sectional views of another example dilator with expandable tabs.
Figure 10B:
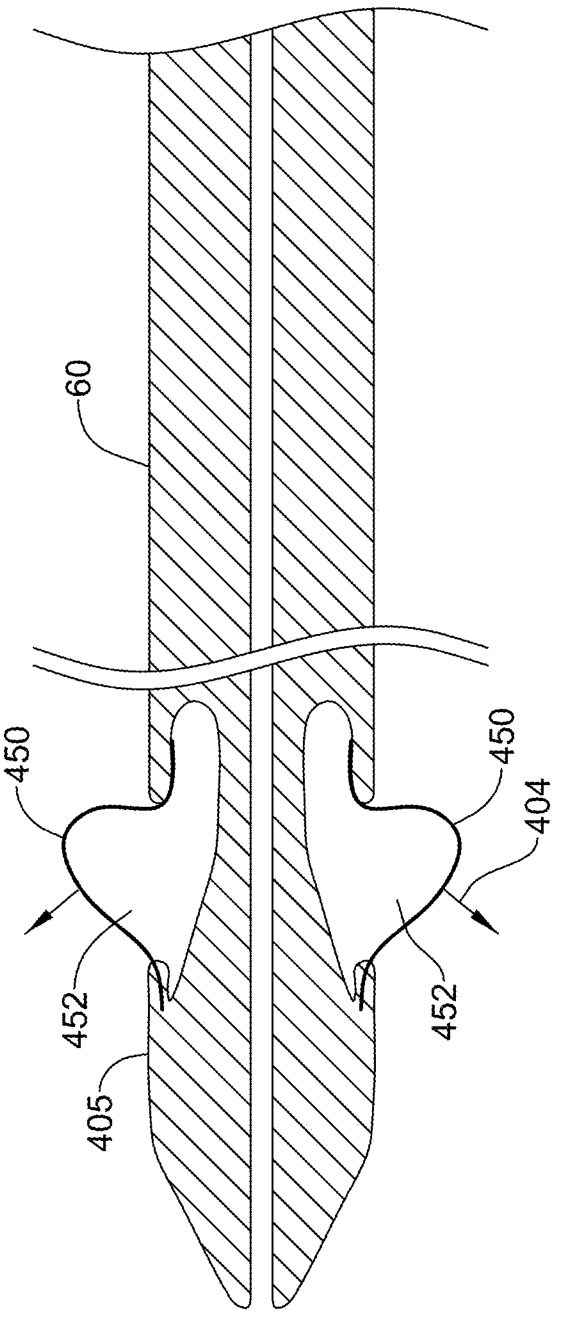
Figure 10C:
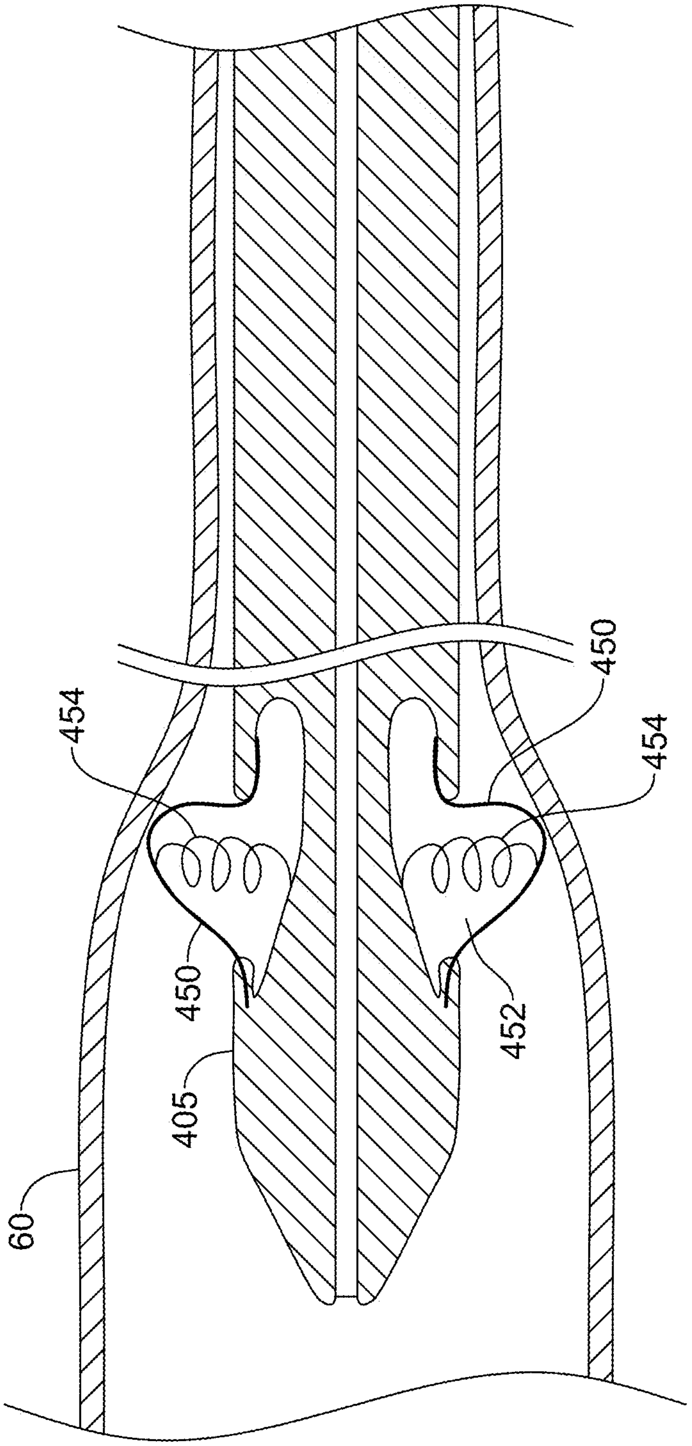

Another example dilator 400 is illustrated in FIGS. 10A-10C. The dilator 400 may include a shaft 405 with a tapered distal tip 420, a lumen 430 extending longitudinally through the entire shaft, and a knob or hub 440 coupled to the proximal end of the shaft, as shown in FIG. 10A. The shaft 405 may include at least one expandable member or tab 450 biased in a radially expanded configuration, but configured to be maintained in a compressed configuration when the dilator 400 is disposed inside an expandable sheath 60 and the tab 450 is not positioned under a fold, such as in the sheath 60 described above. In some examples, when the shaft 405 is disposed within the sheath 60, the tab 450 is in the compressed configuration (FIG. 10A), and the outer diameter of the expandable tab 450 is equal to or less than the outer diameter of the shaft 405. The hub 440 may include one or more visible rotational marker 441 on the outer surface of the proximal end of the shaft 405 or on the hub 440. The marker 441 may be aligned with a tab 450 so the user will know the circumferential position of the tab 450 and can rotate the shaft 405 to position the tab 450 between folds 62 in the sheath 60 for delivery, and rotate the shaft to position the tab 450 under one of the folds 62 for deployment. The expandable tab(s) 450 may also include radiopaque material. Moving the shaft 405 distally out of the sheath 60 causes the tab 450 to move into the expanded configuration (FIG. 10B), in which the outer diameter of the tab 450 is greater that the outer diameter of the shaft 405.

Deployment of the tab 450 may be achieved by moving the shaft 405 distally relative to the sheath 60 until the tab 450 is distal of the distal end of the sheath 60. Without the sheath 60 applying a radially inward compressive force, indicated by arrows 402, the tabs 450 expand to the biased expanded position, as shown in FIG. 10B. The dilator 400 may have a plurality of tabs 450, such as two, three, four, five, six, etc. In some examples, the dilator 400 may include as many tabs 450 as there are folds 62 in the sheath 60. Once the tabs 450 are in the expanded configuration, the shaft 405 may be rotated relative to the sheath 60 to align each tab 450 with a fold 62. As the shaft 405 is then withdrawn proximally into and through the sheath 60, each tab 450 expands its associated fold 62 to expand the sheath 60, as shown in FIG. 10C.

The expandable tabs 450 may be formed from a layer of shape memory material extending over a recess 452 adjacent the distal tip 420, where the layer of material is biased in a radially expanded configuration, as shown in FIGS. 10A and 10B. In other examples, the tabs 450 may be formed as a layer extending over the recess 452, with a spring mechanism 454 disposed in the recess 452 to bias the tabs 450 in the radially expanded configuration, as shown in FIG. 10C. The spring mechanism 454 may be a spring-shaped element as shown in FIG. 10C, or it may be a lever biasing the tab in the radially expanded configuration. In some examples, the tabs 450 may be formed monolithically with the shaft 405, as a layer of shaft material extending over the recess 452. In other examples, the expandable tab 450 may be formed as a fin extending over the spring and fixed to the shaft 405.

Figure 11A:
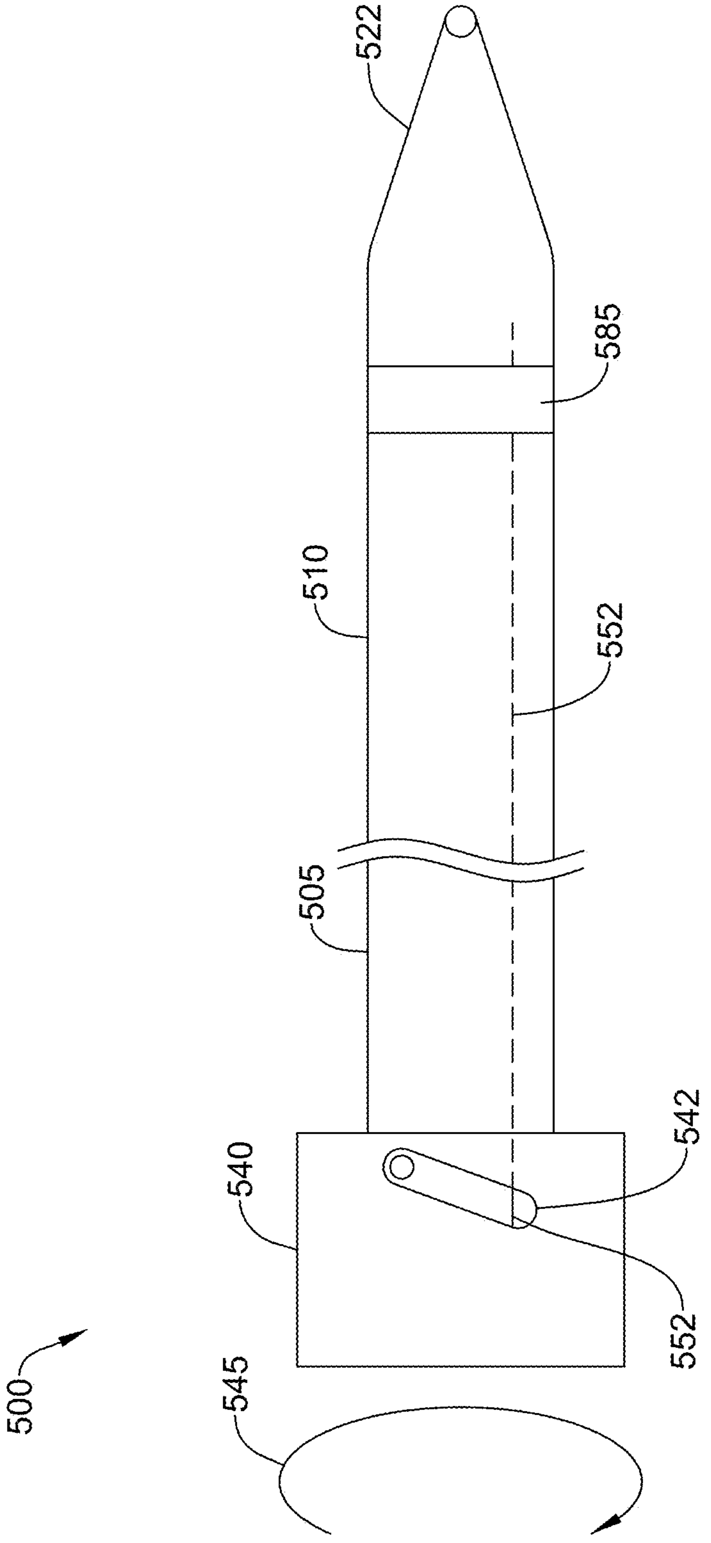
FIGS. 11A and 11B are side partial cross-sectional views of another example dilator with a compressible ring.
Figure 11B:
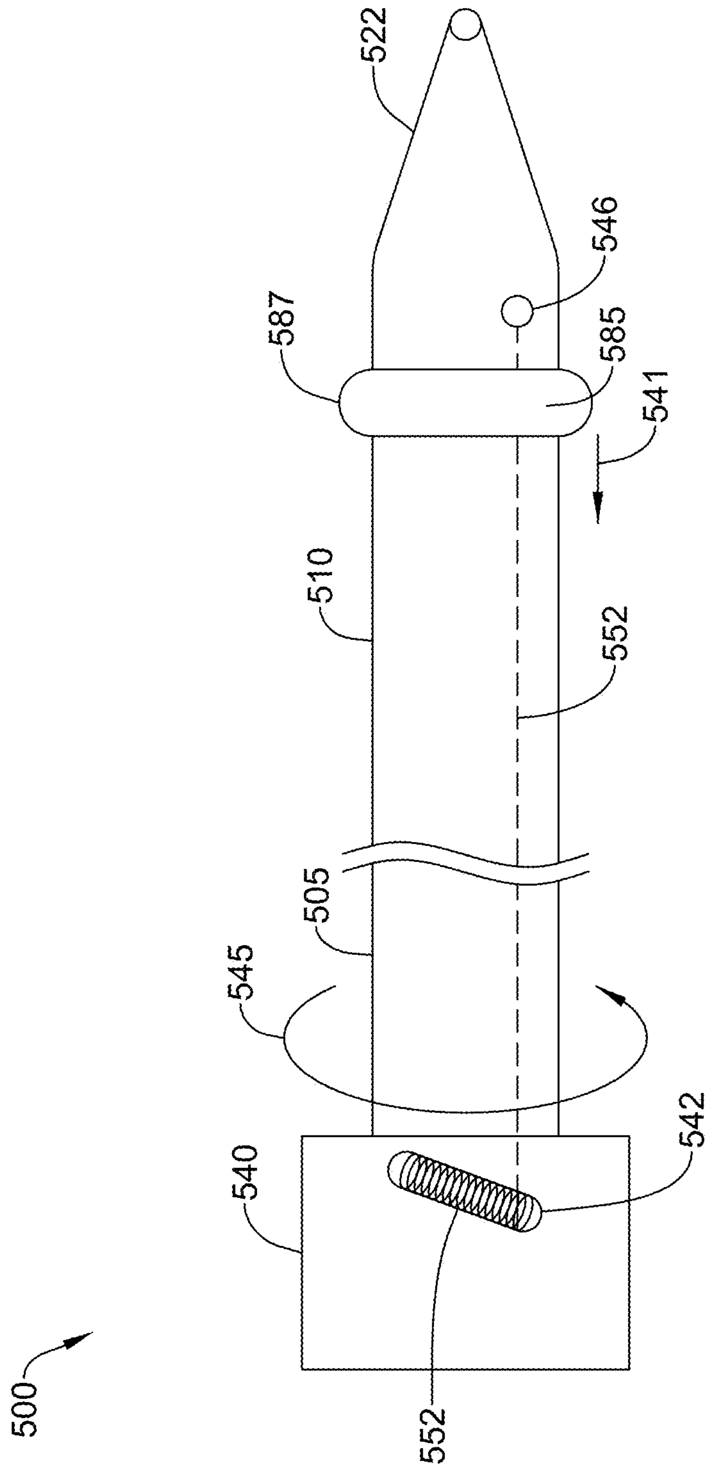

FIGS. 11A and 11B illustrate another embodiment in which the dilator 500 has a shaft 505 with a lumen extending therethrough and a knob 540 rotatably coupled to the proximal end of the shaft, but the tapered distal tip 522 is spaced apart longitudinally from the distal end of the body 510 of the shaft 505 by a compressible ring 585. See FIG. 11A. The shaft 505 may include a tether 552 fixed to an interior of the tapered distal tip 522 and extending through the lumen and out the proximal end of the shaft 505. Pulling the tether 552 proximally relative to the shaft 505 pulls the distal tip 522 axially towards the distal end of the shaft body 510 and axially compresses the compressible ring 585 which causes the outer diameter of the compressible ring 585 to expand and extend radially outward beyond the outer surface of the shaft body 510, forming a circumferential ridge 587, as shown in FIG. 11B. The sheath 60 is not shown in FIGS. 11A and 11B, however similar to the protrusions 382 on the flexible ring 380 and the expandable tab 450 described above, when the compressible ring 585 is in the compressed configuration, the circumferential ridge 587 expands the folds 62 on the sheath 60 when the dilator 500 is pulled proximally into the sheath 60.

In some examples, the tether 552 may be manually pulled proximally to move the distal tip 522 and compress the compressible ring 585. In other examples, a knob 240, 340 as described above with regard to FIGS. 7 and 8 may be coupled to the proximal end of the shaft 505. The knob may be configured to pull the tether 552 proximally relative to the shaft 505. In some examples, the knob 340 may be coupled to the proximal end of the shaft 505 with a frangible connector 215 that is breakable with a twisting or pulling force and the knob 340 is configured to be pulled proximally away from the proximal end of the shaft 505, as shown in FIG. 8.

In the example illustrated in FIGS. 11A and 11B, the dilator 500 includes a rotatable knob 540 rotatably coupled to the proximal end of the shaft 505. The knob 540 may have a continuation of the lumen extending through the shaft 505. A pin 542 may be disposed across the lumen within the knob 540, and a proximal end of the tether 552 may be fixed to the pin 542. Rotation of the knob 540, as indicated by arrow 545, winds the tether 552 around the pin 542 and pulls the tether 552 proximally, thereby pulling the distal tip 522 closer to the distal end of the shaft 505 as indicated by arrow 541, and compressing the compressible ring 585 to form circumferential ridge 587, as shown in FIG. 11B.

Alternatively, the dilator 500 may have a knob as described above in regard to FIG. 7, and the tether 552 may extend through an opening in the side of the knob with the proximal end of the tether fixed to the outer surface of the knob. In this example, rotation of the knob relative to the shaft causes the tether to be wound around the outer surface of the knob, while pulling the distal tip 522 closer to the distal end of the shaft 505 to compress the compressible ring 585 and form circumferential ridge 587.

Figure 12:
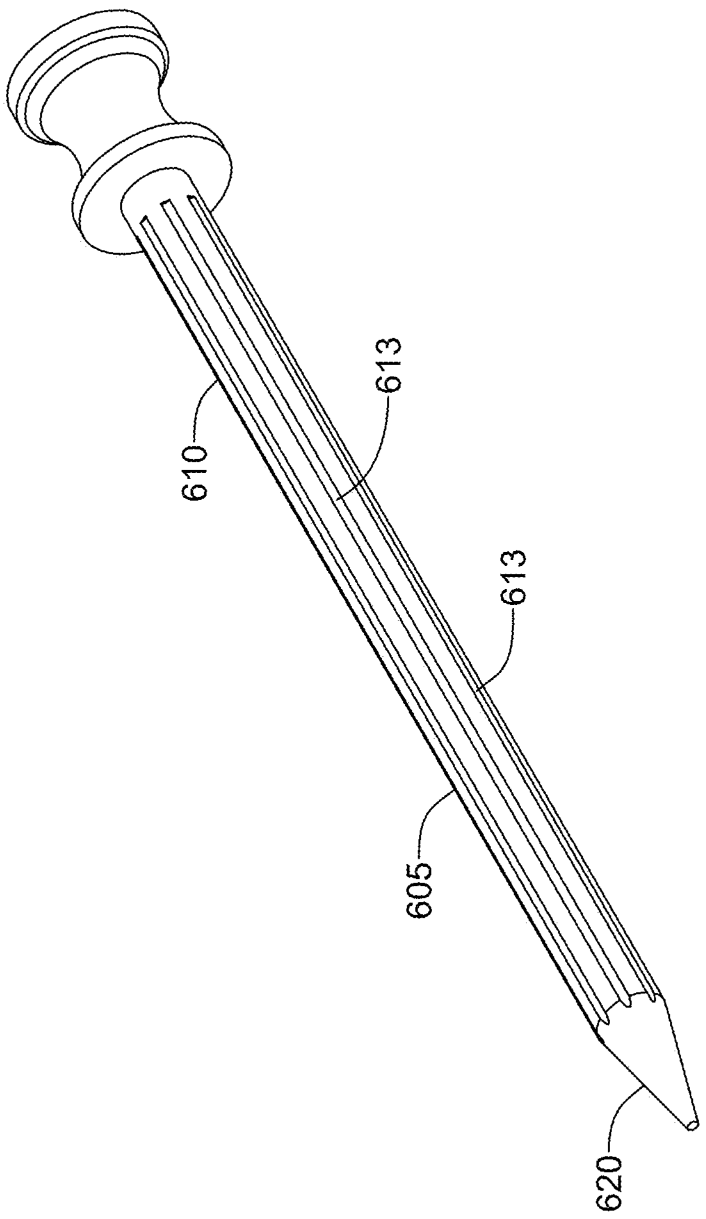
FIG. 12 is a perspective view of an example dilator with channels.

In some examples, any of the shafts 105, 205, 305, 405, 505 described herein may include a plurality of longitudinal channels for allowing blood and/or medication to flow around and along the shaft. FIG. 12 illustrates a dilator shaft 605 with a plurality of channels 613 extending longitudinally along the body 610 of the shaft 605. As shown, the channels 613 extend from the proximal end of the distal tip 620 to the proximal region of the shaft 605. When the shaft 605 is disposed in a body lumen, the channels 613 may allow for blood and/or medication delivered from the proximal end of the shaft, to move along the shaft to and from a position distal of the shaft to the proximal end region of the shaft. The channels 613 may extend partially along the shaft 605, or they may extend along the entire shaft body 610 and onto the proximal end of the distal tip 620.

In some examples, the various elements of the dilator shaft 105, 205, 305, 405, 605 and the sheath 60 may be made of polymer, elastomeric polyamides, block polyamide/ethers, polyether block amide (PEBA, for example available under the trade name PEBAX®), ethylene tetrafluoroethylene (ETFE), or other polymers generally used in medical catheters. The expandable tabs 450 may be made of a shape memory material, such as nitinol or a shape memory polymer. The entire dilator shaft 105 may be formed from a single monolithic piece.

It will be understood that any dimensions described in association with the above figures are illustrative only, and that other dimensions of slits, expanders, and sheaths are contemplated. The materials that can be used for the various components of the dilator for expanding the expandable sheath 60 (and/or other systems or components disclosed herein) and the various elements thereof disclosed herein may include those commonly associated with medical devices. For simplicity purposes, the following discussion refers to the dilator shaft 205 (and variations, systems or components disclosed herein). However, this is not intended to limit the devices and methods described herein, as the discussion may be applied to other elements, members, components, or devices disclosed herein.

In some embodiments, the dilator shaft 205 (and variations, systems or components thereof disclosed herein) may be made from a polymer (some examples of which are disclosed below), a metal, a metal-polymer composite, or other suitable material. Some examples of suitable metals and metal alloys include stainless steel, such as 444V, 444L, and 314LV stainless steel; mild steel; nickel-titanium alloy such as linear-clastic and/or super-elastic nitinol; cobalt chromium alloys, titanium and its alloys, alumina, metals with diamond-like coatings (DLC) or titanium nitride coatings, other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; platinum; palladium; gold; combinations thereof; and the like; or any other suitable material.

In at least some embodiments, portions or all of the dilator shaft 205 (and variations, systems or components thereof disclosed herein) may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the dilator shaft 205 (and variations, systems or components thereof disclosed herein). Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the dilator shaft 205 (and variations, systems or components thereof disclosed herein) to achieve the same result.

In some embodiments, the dilator shaft 205 (and variations, systems or components thereof disclosed herein) and/or portions thereof, may be made from or include a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex® high-density polyethylene, Marlex® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, polyurethane silicone copolymers (for example, Elast-Eon® from AorTech Biomaterials or ChronoSil® from AdvanSource Biomaterials), biocompatible polymers, other suitable materials, or mixtures, combinations, copolymers thereof, polymer/metal composites, and the like. In some embodiments, the sheath can be blended with a liquid crystal polymer (LCP). For example, the mixture can contain up to about 6 percent LCP.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. An expandable dilator, comprising:

a shaft having a tapered distal tip, a body, a proximal end, and a lumen extending longitudinally from the tapered distal tip to the proximal end, the shaft including a cutout through a sidewall of the shaft adjacent the tapered distal tip, and a slit extending through the sidewall and extending from the cutout to the proximal end;

an expander positioned within the cutout, the expander having an outer diameter larger than an inner diameter of the lumen such that a portion of the expander extends through the cutout, the expander including a tether fixed to the expander and extending through the lumen and exiting out the proximal end of the shaft; and wherein pulling the tether proximally moves the expander proximally through the shaft such that the expander separates opposing edges of the slit as the expander moves proximally through the shaft.

2. The expandable dilator of claim 1, wherein a proximal end of the tether is fixed to a knob coupled to the proximal end of the shaft, the knob configured to pull the tether and the expander proximally through the shaft.

3. The expandable dilator of claim 2, wherein the knob is configured to be pulled proximally away from the proximal end of the shaft.

4. The expandable dilator of claim 3, wherein the knob is coupled to the shaft with a frangible connector that is breakable with a twisting or pulling force.

5. The expandable dilator of claim 2, wherein the knob is rotatably coupled to the proximal end of the shaft, and the tether is fixed to the knob such that rotation of the knob relative to the shaft in a first direction winds the tether onto the knob as the expander is pulled proximally through the lumen.

6. The expandable dilator of claim 1, wherein the shaft includes a plurality of channels extending longitudinally along an entirety of the shaft from a proximal end of the tapered distal tip.

7. A dilation system, comprising:

the expandable dilator of claim 1; and an expandable sheath having a distal end, a proximal end, a lumen extending therebetween, and at least one fold extending longitudinally from the distal end to the proximal end, each fold defined by a circumferential overlap of material forming the expandable sheath, the expandable sheath including a distal ring configured to hold the expandable sheath in a compressed configuration, the distal ring having a longitudinal slit disposed over the fold, the distal ring biased in a closed configuration and expandable to an expanded configuration in which the slit is expanded when the expandable dilator is disposed within the expandable sheath with the expander positioned distal of the distal end of the expandable sheath, and the expander of the expandable dilator is pulled proximally, thereby allowing the fold to unfold and expand an inner diameter of the expandable sheath.

8. A dilator for use with an expandable sheath, the dilator comprising:

a shaft having a tapered distal tip, a proximal end;

a flexible ring disposed around the tapered distal tip, the flexible ring configured to be moved axially from the tapered distal tip onto the shaft, the flexible ring having a plurality of protrusions extending radially outward from an outer surface of the flexible ring; and at least one tether having a distal end fixed to the flexible ring and a proximal end extending axially along an outer surface of the tapered distal tip and into an opening in the shaft, the tether extending through a lumen of the shaft, wherein the proximal end of the at least one tether extends proximally out of the proximal end of the shaft.

9. The dilator of claim 8, wherein the at least one tether includes two tethers fixed to opposite sides of the flexible ring, wherein the opening in the shaft includes two openings disposed on opposite sides of the shaft, wherein each tether extends into one of the two openings.

10. The dilator of claim 8, wherein the plurality of protrusions are ridges extending longitudinally along the outer surface of the flexible ring.

11. The dilator of claim 8, wherein the opening is disposed on the shaft such that when the flexible ring is pulled onto the shaft, the opening is adjacent a proximal end of the flexible ring.

12. An expandable dilator for use with an expandable sheath, comprising:

a shaft having a tapered distal tip and a body with a proximal end, and a lumen extending longitudinally therethrough;

at least one expandable member disposed on the body of the shaft, each expandable member configured to move from a compressed configuration to an expanded configuration, wherein when in the compressed configuration an outer diameter of the expandable member is equal to or less than an outer diameter of the body, wherein when in the expanded configuration the outer diameter of the expandable member is greater that the outer diameter of the body; and wherein when the shaft is disposed within the expandable sheath, the expandable member is in the compressed configuration, and moving the shaft distally out of the expandable sheath causes the expandable member to move into the expanded configuration.

13. The expandable dilator of claim 12, wherein the shaft includes at least one recess on the body, and the expandable member extends over the recess.

14. The expandable dilator of claim 13, wherein the expandable member is formed of a shape memory material and is biased in the expanded configuration.

15. The expandable dilator of claim 13, wherein the recess includes a spring and the expandable member extends over the spring.

16. The expandable dilator of claim 12, wherein the shaft includes at least one rotational marker on the proximal end indicating a circumferential position of the expandable member.

17. The expandable dilator of claim 12, wherein the expandable member includes a compressible ring disposed between the tapered distal tip and the body, the shaft including a tether fixed to an inner wall of the tapered distal tip and extending through the lumen and out the proximal end of the shaft, wherein pulling the tether proximally relative to the shaft pulls the tapered distal tip towards a distal end of the body and compresses the compressible ring such that an outer diameter of the compressible ring extends radially outward beyond an outer surface of the body, forming a circumferential ridge.

18. The expandable dilator of claim 12, further comprising a knob coupled to the proximal end of the shaft, the knob configured to pull the tether proximally relative to the shaft.

19. The expandable dilator of claim 18, wherein the knob is coupled to the proximal end of the shaft with a frangible connector that is breakable with a twisting or pulling force wherein the knob is configured to be pulled proximally away from the proximal end of the shaft.

20. The expandable dilator of claim 18, wherein the knob is rotatably coupled to the proximal end of the shaft, and the tether is fixed to the knob such that rotation of the knob relative to the shaft in a first direction winds the tether onto the knob as the tapered distal tip is pulled proximally.

* * * * *